(12) United States Patent
Sheu et al.

(10) Patent No.: US 7,909,864 B2
(45) Date of Patent: Mar. 22, 2011

(54) IMPLANTABLE MEDICAL DEVICES HAVING ADJUSTABLE PORE VOLUME AND METHODS FOR MAKING THE SAME

(75) Inventors: Min-Shyan Sheu, Chelmsford, MA (US); Steve Walak, Natick, MA (US); Yixin Xu, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/166,377

(22) Filed: Jul. 2, 2008

(65) Prior Publication Data
US 2009/0012603 A1   Jan. 8, 2009

Related U.S. Application Data

(60) Provisional application No. 60/948,254, filed on Jul. 6, 2007.

(51) Int. Cl.
*A61F 2/06* (2006.01)
(52) U.S. Cl. ............... 623/1.42; 623/1.15; 623/1.46
(58) Field of Classification Search ............ 623/1.15, 623/1.39, 1.42, 1.44, 1.46; 606/191
See application file for complete search history.

(56) References Cited

U.S. PATENT DOCUMENTS

| | | | |
|---|---|---|---|
| 6,096,070 A * | 8/2000 | Ragheb et al. | 623/1.39 |
| 2002/0111601 A1 | 8/2002 | Thompson | |
| 2005/0271696 A1 | 12/2005 | Dinh et al. | |
| 2007/0055274 A1 * | 3/2007 | Appenzeller et al. | 606/90 |
| 2007/0293885 A1 * | 12/2007 | Binmoeller | 606/191 |

FOREIGN PATENT DOCUMENTS

| | | |
|---|---|---|
| EP | 0 712 615 A1 | 5/1996 |
| WO | 00/32255 A1 | 6/2000 |
| WO | 2007/010536 A2 | 1/2007 |

OTHER PUBLICATIONS

Communication Relating to the Results of the Partial International Search (Annex to Form PCT/ISA/206), mailed Dec. 17, 2009, from related International Application No. PCT/US2008/068958.
International Search Report and Written Opinion of the International Searching Authority, mailed Jan. 20, 2010, from related International Application No. PCT/US2008/068958.

* cited by examiner

*Primary Examiner* — Corrine M McDermott
*Assistant Examiner* — Matthew Schall
(74) *Attorney, Agent, or Firm* — Kenyon & Kenyon LLP (57) ABSTRACT

The present invention is directed to implantable medical devices which may be used for controllably releasing a therapeutic agent within a patient and methods for making the same. These medical devices may include porous coatings, which may be polymer-free, located on an outer surface or abluminal surface of the medical device. The medical device may be a stent. The pores of the porous coating may be expandable to facilitate loading of the therapeutic agent. The medical device may be triggerable upon implantation of the medical device such that the volume of the voids shrinks to eject the therapeutic agent. The voids may be slots in the stent. Expandable materials or structures may be positioned in the voids to expand upon implantation and eject the therapeutic agent.

7 Claims, 9 Drawing Sheets

Providing a Medical Device
Step 400

Applying a Coating to an Outer Surface of the Medical Device. The Coating May Include a Plurality of Pores.
Step 410

Expanding the Coating to Increase a Pore Size of the Pores From a First Size to a Second Size
Step 420

Loading the Pores With Therapeutic Agent While the Pore Size is Expanded
Step 430

Providing a Medical Device
Step 800

Applying a Porous Coating Having a Plurality of Pores to an Outer Surface of the Medical Device
Step 810

Loading the Pores With a First Layer Comprised of an Expandable Material
Step 820

Loading the Pores With a Second Layer Comprised of Therapeutic Agent
Step 830

Providing a Medical Device Having a Plurality of Struts. Each Strut may Have an Inner Surface and Outer Surface
Step 1300

Cutting a Plurality of Slots Extending Between the Inner and Outer Surfaces of the Plurality of Slots
Step 1310

Applying a First Porous Coating Into the Slot.
Step 1320

Positioning an Expandable Member Onto the First Porous Coating
Step 1330

Applying a Therapeutic Agent Layer Which may Comprise Therapeutic Agent Onto the Expandable Member
Step 1340

Applying a Second Porous Coating
Step 1350

FIG.13

IMPLANTABLE MEDICAL DEVICES HAVING ADJUSTABLE PORE VOLUME AND METHODS FOR MAKING THE SAME

CROSS REFERENCE TO RELATED APPLICATION

The present application claims priority to U.S. provisional application Ser. No. 60/948,254 filed Jul. 6, 2007, the disclosure of which is incorporated herein by reference in its entirety.

TECHNICAL FIELD

The present invention generally relates to implantable medical devices for delivering therapeutic agent.

BACKGROUND

The positioning and deployment of medical devices within a target site of a patient is a common, often repeated procedure of contemporary medicine. These devices, which may be implantable stents, cardiac rhythm management leads, neuromodulation devices, implants, grafts, defibrillators, filters, catheters and the like, may be deployed for short or sustained periods of time. They may be used for many medical purposes including the reinforcement of recently re-enlarged lumens, the replacement of ruptured vessels, and the treatment of disease through local pharmacotherapy. They may also be deployed in various areas of the body including the coronary vasculature, the peripheral vasculature, the cerebral vasculature, the esophagus, the trachea, the colon, and the biliary tract.

Porous and/or non-porous coatings may be applied to the surfaces of these medical devices to increase their effectiveness. These coatings may provide a number of benefits including reducing the trauma suffered during the insertion procedure, facilitating the acceptance of the medical device into the target site, and improving the post-procedure effectiveness of the device.

Coated medical devices may also provide for the localized delivery of therapeutic agents to target locations within the body. Such localized drug delivery avoids the problems of systemic drug administration, producing unwanted effects on parts of the body that are not to be treated, or not being able to deliver a high enough concentration of therapeutic agent to the afflicted part of the body. Localized drug delivery may be achieved, for example, by coating portions of the medical devices that directly contact the inner vessel wall. This drug delivery may be intended for short and sustained periods of time.

BRIEF DESCRIPTION

The present invention generally relates to medical devices that may be configured for controlled drug delivery to target sites of a patient. The drug to be delivered may be in a coating located on an outer surface that may be positioned on the device prior to use. The coating may have pores or other voids that may change in volume. The coating may be applied on the outer surface of the device and can have first and second layers. The first layer may include an expandable material while the second layer may be comprised of material having a plurality of pores. The coating may also include individual voids with active components that urge therapeutic agent stored in the voids outward after the device is deployed at a target site.

The present invention also includes methods for making a medical device with adjustable pore volumes. These methods may comprise applying a coating having multiple layers to an outer surface of a medical device wherein one layer may comprise a material having a plurality of pores and another layer may comprise a material that expands and contracts with temperature change. The method may also include expanding the lower layer to increase the size of pores of the upper layer and loading the expanded pores with therapeutic agent. After loading, the lower layer may contract, shrinking the upper layer as well.

Another method in accordance with the present invention may comprise providing a porous coating having a plurality of pores to an outer surface of a medical device. The pores may be packed with an expandable material below a layer comprised of therapeutic agent. The therapeutic agent loaded in these pores may be deployed when the lower material expands, shrinking the volume of the pore.

The porous coatings of medical devices of the present invention may be selectively applied in specified areas or regions of the medical device and any number of porous coatings may be applied. In each of the cases described, the voids and interstices of the porous coating may be configured and adjustable to control the elution rate of the therapeutic agent.

Thus, the invention may be embodied by numerous devices and methods. The description provided herein, when taken in conjunction with the annexed drawings, discloses examples of the invention. Other embodiments, which incorporate some or all steps as taught herein, are also possible.

BRIEF DESCRIPTION OF THE DRAWINGS

Referring to the drawings, which form a part of this disclosure:

FIG. 2b shows a system that may be employed in accordance with embodiments of the present invention for expanding and loading the medical device of FIG. 2a;

FIG. 3b shows a system that may employed in accordance with embodiments of the present invention for expanding and loading the medical device of FIG. 3a;

DETAILED DESCRIPTION

The present invention generally relates to medical devices having porous coatings or slots that may be configured for drug delivery and methods for making the same. The applied coatings or slots may comprise voids or interstices of various sizes, including some or all having dimensions in a nanometer or a micrometer scale. These voids or interstices may be adjustable in volume to facilitate the loading, storage, and release of therapeutic agent from the medical device. For example, the size of a pore opening may be expanded to accommodate loading and then contracted back to a resting state to accommodate transport and delivery. Similarly, the coating may comprise various layers, one of which stores therapeutic agent and acts to pump the therapeutic agent through an outer coating as the device is deployed. Still further, the coatings may contain voids with active sides that work to dispense therapeutic agent from the void when the device is within the body.

In the case of an implanted stent with an outer porous coating, elution of the therapeutic agent may be triggered by changing the pore size in vivo. For example, the trigger mechanisms for the release of the therapeutic agent may include temperature (from room to body), vibration, and bodily fluids (e.g., water content, pH, and ions). In some instances, the coating is polymer free and, thus, may eliminate any potentially inflammatory reactions associated with the use of polymers on medical devices.

Figure 1A:
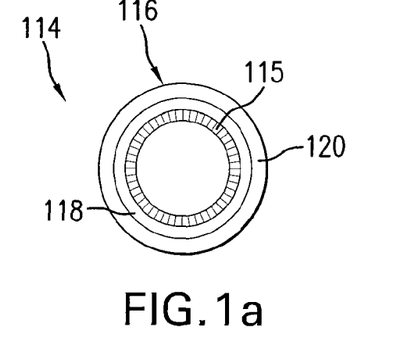
FIG. 1a shows an end view of a medical device including a coating having first and second layers as may be employed in accordance with embodiments of the present invention.
Figure 1B:
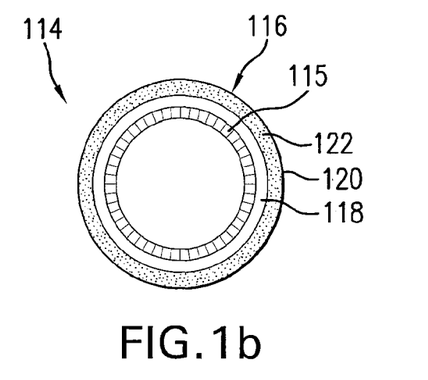
FIG. 1b shows the medical device of FIG. 1a with the first and second layers expanded and the second layer having therapeutic agent loaded therein.
Figure 1C:
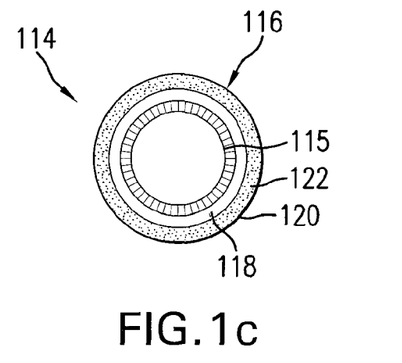
FIG. 1c shows the medical device of FIGS. 1a-b with the first and second layers contracted after loading of the therapeutic agent.

Referring initially to FIGS. 1a-c, a medical device 114 may be provided comprising an elongate tubular body 115 having inner and outer surfaces. A coating 116 may be applied on the outer surface and can have first and second layers 118, 120. The first layer 118 may include an expandable material and the second layer 120 may be comprised of a material having a plurality of pores configured for loading with a therapeutic agent 122.

FIG. 1a shows the medical device 114 and the first and second layers 118, 120 in a contracted position. FIG. 1b shows the medical device 114 in an expanded position following loading of the second layer 120 with therapeutic agent 122. FIG. 1c shows the medical device 114 in an unexpanded position with the second layer 120 loaded with therapeutic agent 122.

Figure 2A:
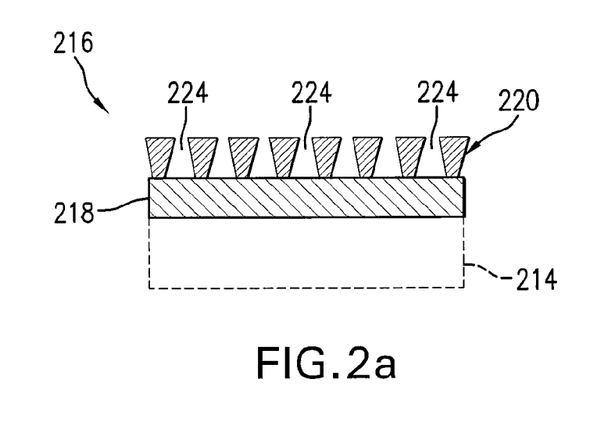
FIG. 2a shows an enlarged cross-sectional view of a portion of a coating having first and second layers as may be employed in accordance with embodiments of the present invention.

FIG. 2a shows a cross-sectional view of a portion of coating 216 with first and second layers 218, 220. The first, or bottom, layer 218 can be a solid material, such as a metal, with a relatively high thermal expansion coefficient. The second, or top, layer 220 may be a porous material which can face a wall of a vessel lumen of a patient following deployment of the medical device 214 in vivo.

Figure 2B:
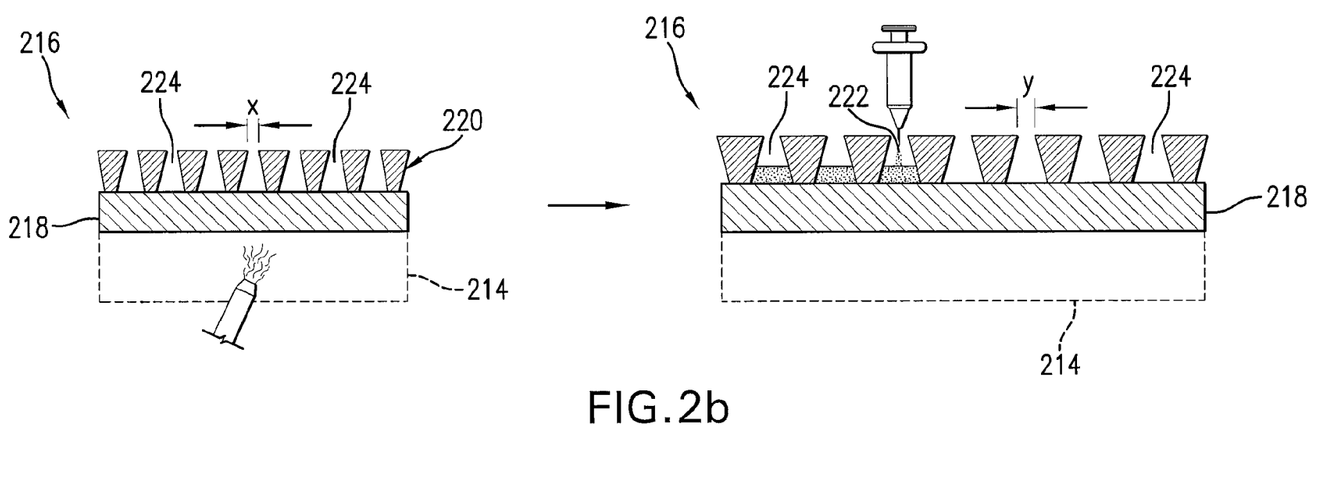

As can be seen in the example of FIG. 2b, the first layer 218 may be indirectly or directly heated using conventional heating techniques (e.g., positioning in a heated solution containing the therapeutic agent) to any suitable temperatures which do not degrade the characteristics of the therapeutic agent. Following the application of heat, the first layer 218 can expand. As the first layer 218 expands, the second layer 220, which may be disposed on top of the first layer 218, may also expand. Thus, pores 224 which comprise the second layer 220 may expand from a first pore size (x) to a second pore size (y), with the second pores size (y) being larger than the first pore size (x). As seen in FIG. 2b, when the pores 224 are in the expanded state, the pores 224 may be loaded with therapeutic agent 222. In the example, the pores 224 are being loaded by an injection device, however, any suitable loading techniques may be used. It will be appreciated that the invention allows the use of porous coatings 220 that may be made of materials other than polymers, e.g., metals, ceramics, or bio-ceramics. The pores of the porous coating may also be formed within an open network of fibers (e.g., fine fibers) attached to the device. Also, because the pore size is increased for drug loading, it may then be contracted to reduce the size of the pore opening for implantation. In this way, the rate of drug elution after implantation may be sustained longer.

In FIG. 2b, increased temperature may be used to increase pore size. In accordance with embodiments of the present invention, it is also contemplated that in certain instances using different materials, a decrease in temperature may be used to increase pore size during loading. For example, in other embodiments, liquid nitrogen immersion may be used to shrink the materials which comprise the second layer to expand the pores for loading.

Porous coatings may be difficult to load with large amounts of therapeutic agent and/or they may be difficult to deliver therapeutic agent from a porous coating over extended periods of time. In order to facilitate loading of the porous coatings with therapeutic agent, solvents and/or surfactants can be used to reduce surface tension and/or viscosity to facilitate entry of the therapeutic agent solvent mixture into the pore. One can also use changes in pressure and temperature to assist in loading therapeutic agent. Further, a porous coating having a larger average pore size may be used to facilitate drug loading, however, larger pore sizes may result in faster release of the therapeutic agent. Thus, the reduction in pore size after loading can be beneficial if slower release is desired.

Figure 3A:
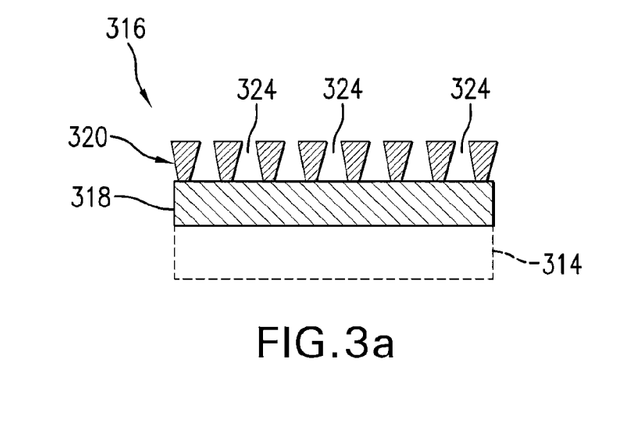
FIG. 3a shows an enlarged cross-sectional view of a portion of a coating having first and second layers as may be employed in accordance with embodiments of the present invention.

FIG. 3a shows a cross-sectional view of a portion of coating 316 with first and second layers 318, 320 in accordance with embodiments of the present invention. The first layer 318 can be a solid material with a relatively high elasticity and/or shape memory characteristics. For example, a sheath of tubular shaped nitinol may be used in the example as the first layer 318. Other titanium alloys such as Flexium™, manufactured by Memory Corporation, and stainless steel may be used. For instance, the tubular shaped sheath may be placed over the medical device 314. The second or top layer 320 may be comprised of a porous material having pores and may face the lumen wall following deployment of the medical device 314 in vivo.

Figure 3B:
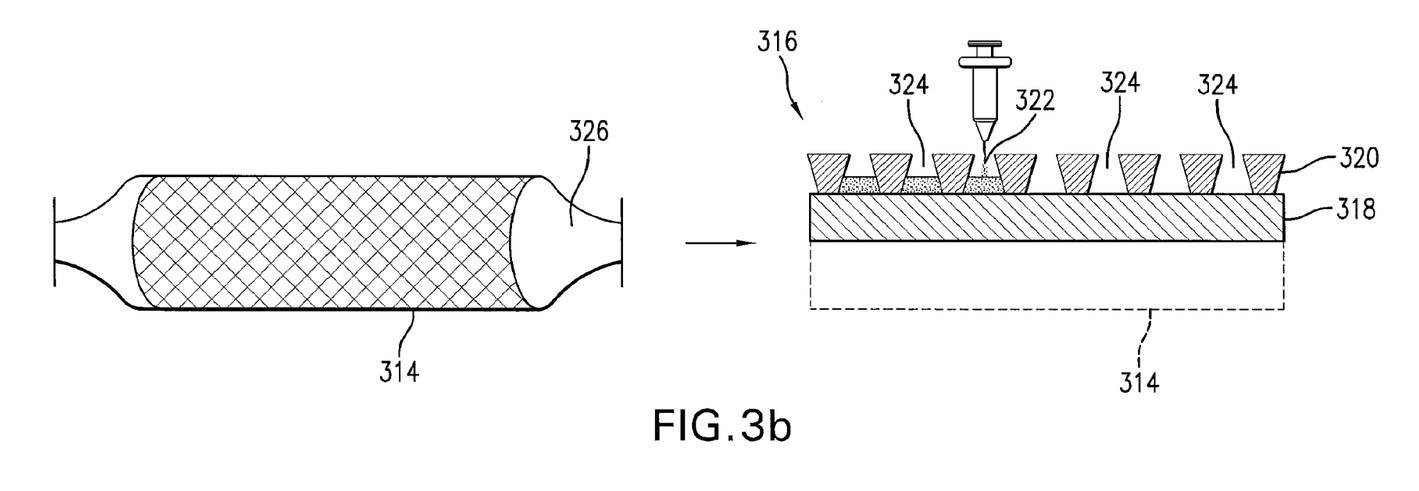

As may be seen in FIG. 3b, an expansion member 326, in this case a balloon such as those used with angioplasty catheters, may be inserted into the first layer 318 and/or medical device 314 for expansion during loading. The expansion of the first layer 318 may in turn increase the size of the pores 324 of the second layer. Accordingly, the therapeutic agent 322 may be loaded into the pores 324. Once the pores 324 are loaded with the therapeutic agent 322, the expansion member 326, in this case the balloon, may be deflated and the first and second layers 318, 320, including the pores 324, may return to their original sizes.

It is also contemplated by embodiments of the present invention that a first layer 218, 318 comprised of a material and/or materials exhibiting both thermal expansion (FIG. 2*a-b*) and elasticity/shape memory (FIG. 3*a-b*) characteristics may be used.

Figure 4:
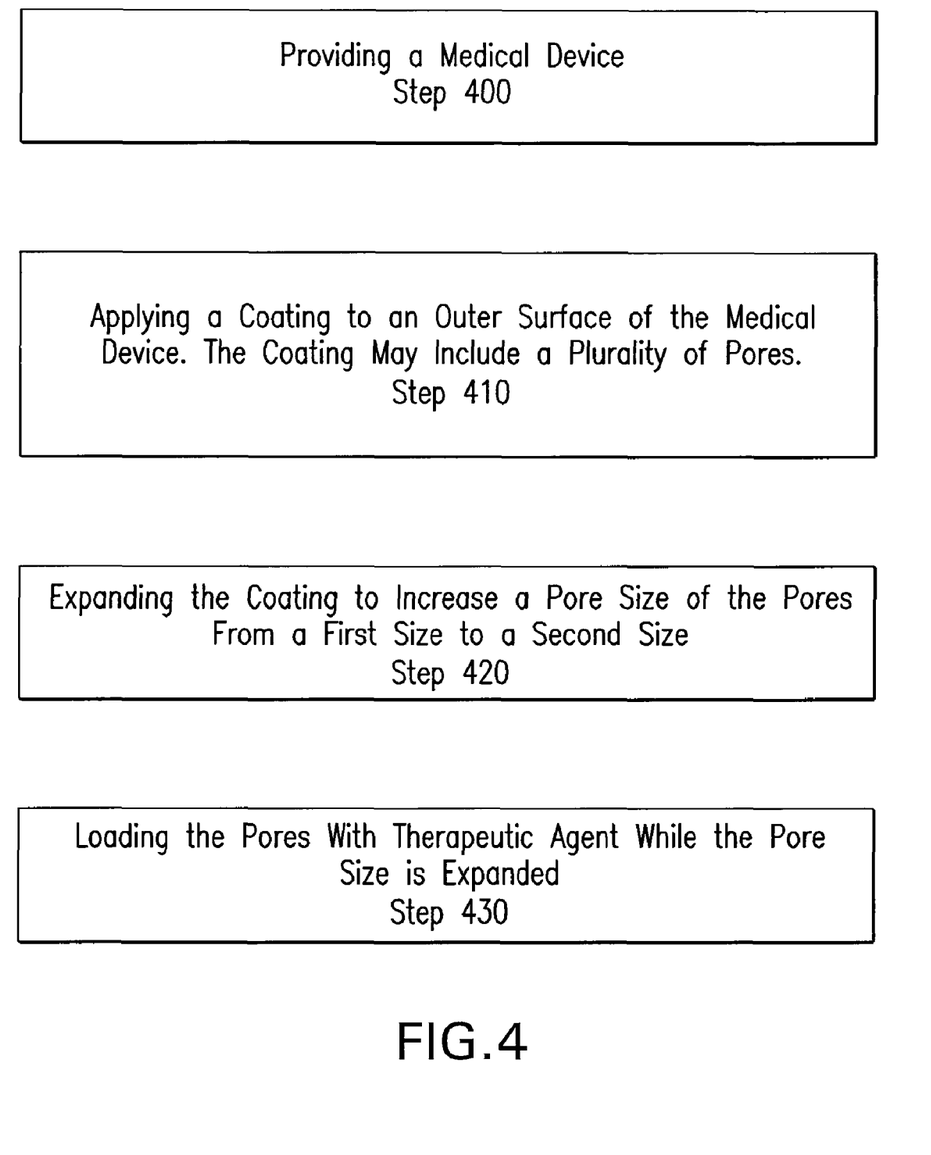
FIG. 4 shows a flow chart of a method that may be employed in accordance with embodiments of the present invention.

FIG. 4 shows a flow chart including method steps that may be employed with embodiments of the present invention. In the example of FIG. 4, step 400 may include providing a medical device and step 410 may include applying a coating to an outer surface of the medical device. The coating may include a plurality of pores. In the embodiments illustrated in FIGS. 1-3, the coating includes first and second layers, with the second layer 120, 220, 320 comprised of a material having a plurality of pores and located on top of the first layer 118, 218, 318. It will be appreciated, however, that a single porous layer may be used and the medical device itself may be used as the expandable material to open or reduce the pore size. Step 420 can include expanding the coating to increase a pore size of the pores from a first size to a second size. Step 430 may include loading the pores with the therapeutic agent while the pore size is expanded.

In other embodiments, the sequence of steps may be reordered and steps may be added or removed. The steps may also be modified consistent with the invention.

Figure 5:
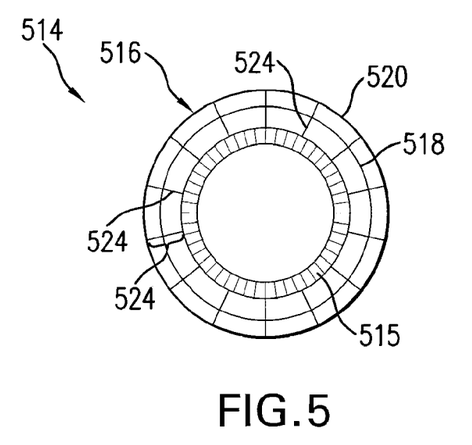
FIG. 5 shows an end view of a medical device having a porous coating with a plurality of pores having first and second layers as may be employed in embodiments of the present invention.

In accordance with other embodiments of the present invention, FIG. 5 shows a medical device 514 having tubular body 515 and a porous structure or coating 516 comprised of a plurality of pores 524. In this example, each pore 524 has a first and second layer 518, 520, however, other arrangements are possible. For example, only some of the pores 524 may be provided with first and second layers 518, 520. In the example, the first layer 518 may be comprised of an expandable material and the second layer 520 may be comprised of a coating including therapeutic agent. Any suitable expandable material may be used, for example, expandable metals, alloys, and polymers can be used. The expansion material may be loaded into the pores 524 with conventional loading techniques prior to loading the pores 524 with the second layer 520.

Figure 6A:
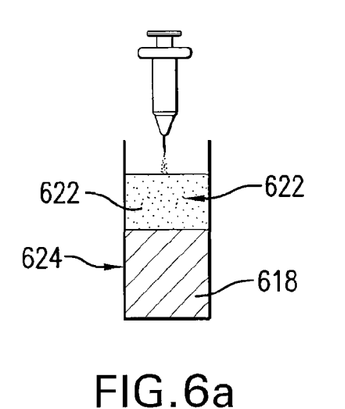
FIGS. 6a-b and 7a-c show enlarged views of pores having a first layer comprised of an expandable material and a second layer comprised of a therapeutic agent as may be employed in accordance with embodiments of the present invention.
Figure 6B:
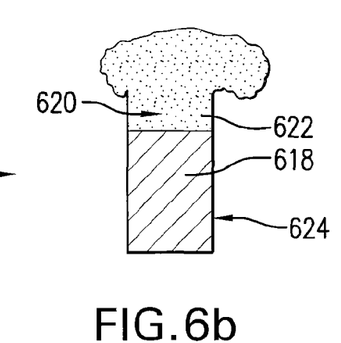

In FIG. 6*a* it can be seen that the coating, including therapeutic agent 622, may be loaded on top of the first layer 618 to form the second layer 620. As is best seen in FIG. 6*b*, when the medical device is positioned in vivo, the first layer 618 may expand. The expansion may be triggered by several factors including, but not limited to, temperature (e.g., room temperature to body temperature) to assist in ejecting the therapeutic agent 622 from the pore 624. Since the expansion member may force or eject the therapeutic agent, it is contemplated by embodiments of the present invention that expansion members may be used with therapeutic agents which may not diffuse in bodily fluids.

Figure 7A:
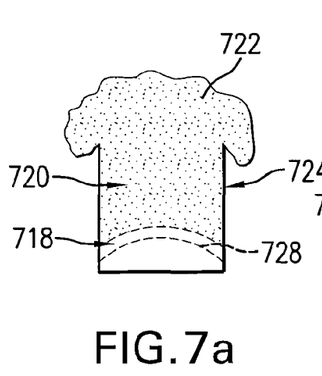
Figures 7B, 7C:
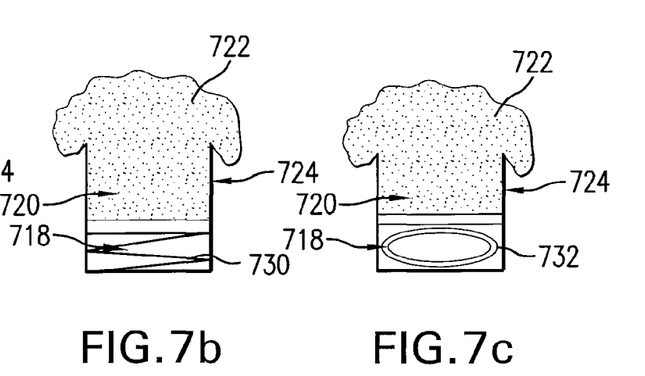

FIGS. 7*a-c* show other expandable materials that may loaded into the pore 724 to form the first layer 718 as may be employed in accordance with embodiments of the present invention. For example, pre-shaped thermal memory alloys, which will be described in more detail below with reference to FIGS. 11*a-c*, may be used. FIG. 7*a* shows a curved sheet 728 that may curve at body temperature. FIG. 7*b* shows a zig-zag shaped sheet 730 that may unfold at body temperature. FIG. 7*c* shows a round tube 732 that may expand at body temperature.

Other suitable expansion members may include compressible fibers and foams, for example, three dimensional compressible fibers and foams may be loaded into compressible metal and/or polymer materials to hold the therapeutic agent. Compacted SMA fibers, as are well known in the art, may also be used.

One-way and two-way shape memory activation may also be used to pull and/or push the therapeutic agent into/out of the pores to facilitate drug loading and release.

Figure 8:
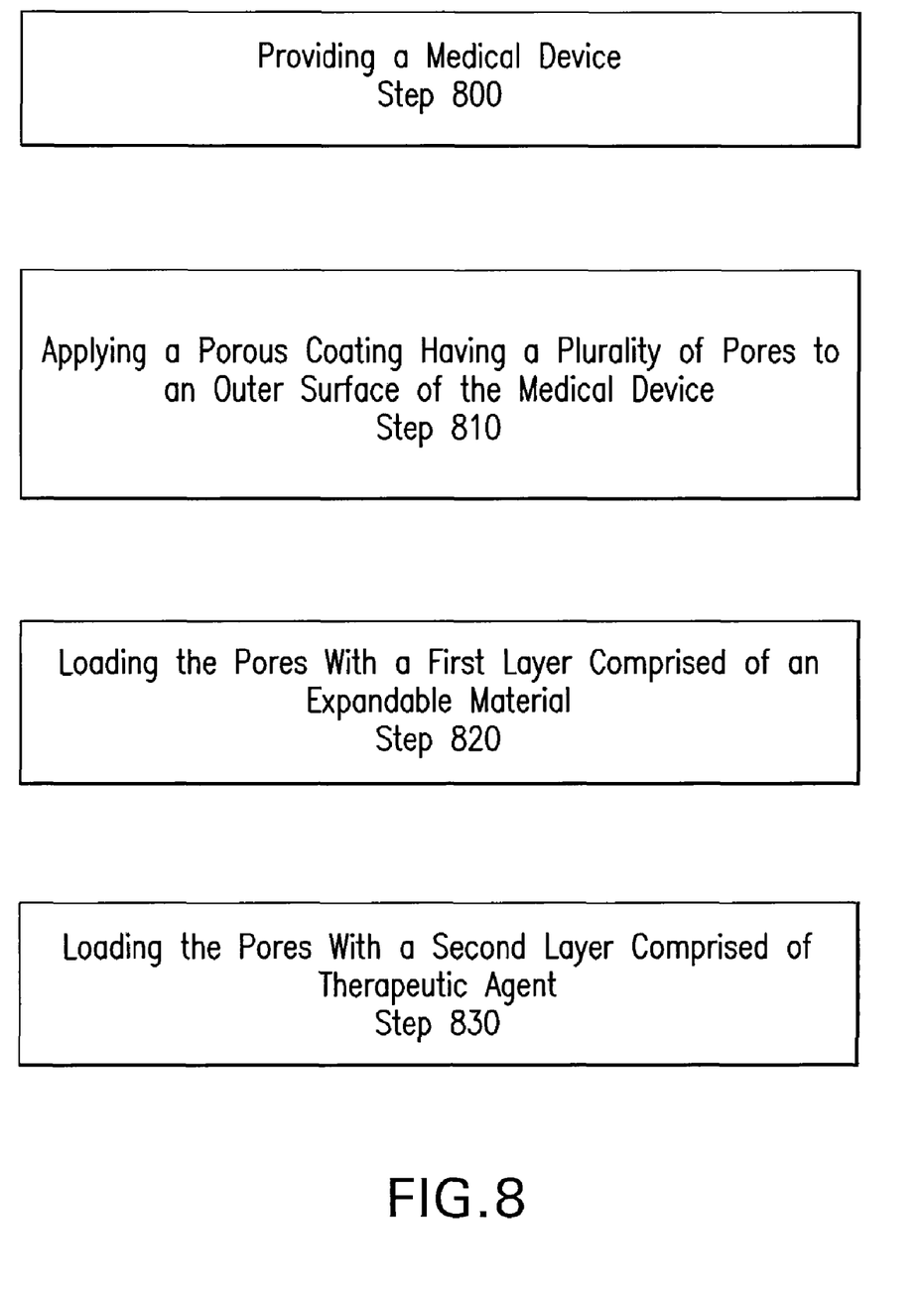
FIG. 8 shows a flow chart of a method that may be employed in accordance with embodiments of the present invention.

FIG. 8 shows a flow chart including method steps that may be employed with embodiments of the present invention for making the medical devices of FIGS. 5-7. In the example of FIG. 8, step 800 may include providing a medical device. Step 810 may include applying a porous coating having a plurality of pores to an outer surface of the medical device. Step 820 may include loading the pores with a first layer comprised of an expandable material and step 830 may include loading the pores with a second layer comprised of the therapeutic agent.

In other embodiments, the sequence of steps may be reordered and steps may be added or removed. The steps may also be modified consistent with the invention.

Figure 9:
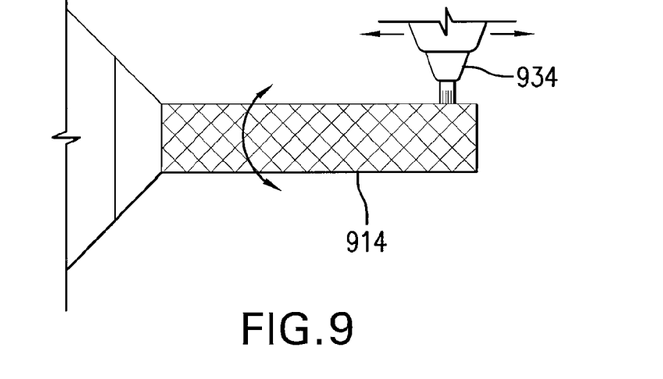
FIG. 9 shows a system for cutting slots into struts of a stent as may be employed in accordance with embodiments of the present invention.

In accordance with other embodiments of the present invention, FIG. 9 shows a stent 914 including a plurality of struts into which slots may be cut, for example by using a conventional laser cutting device 934.

Figure 10A:
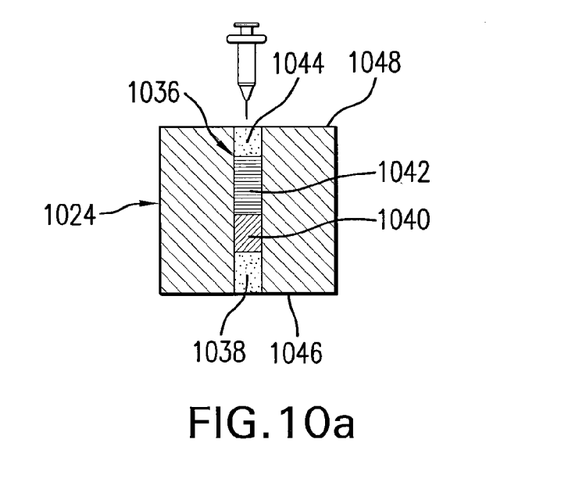
FIGS. 10a-b show an enlarged cross-sectional view of a stent strut slot during loading and then release of a therapeutic agent as may be employed in accordance with embodiments of the present invention.
Figure 10B:
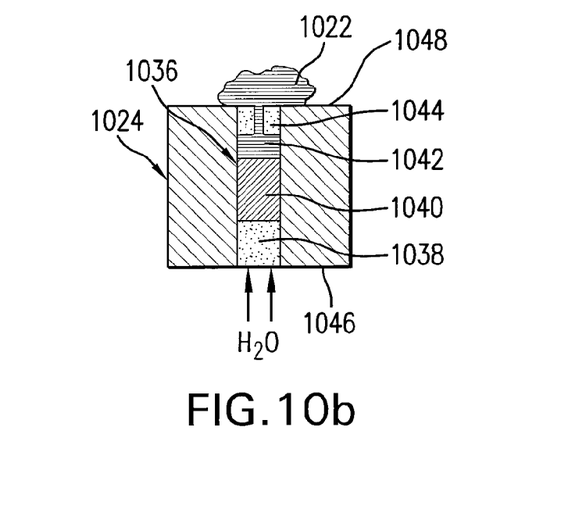

As seen in the examples of FIGS. 10*a-b*, the slot 1036 may be cut into the middle of the struts 1024. Once the slots 1036 are cut, the slots 1036 may be filled with various materials. It will be appreciated that the term "slot" as used herein is meant to encompass any opening of suitable size (e.g., submicron to hundreds of microns) and shape (e.g., square, rectangular, round, cylindrical, etc.). For example, in certain embodiments of the present invention the slot may comprise a hole bored in center portion of the strut and filled with an expandable material or structure and therapeutic agent; however, the slot need not go all of the way through the strut. In other embodiments of the present invention, the slot may comprise a hole bored from the outer surface and filled with an expandable material or structure and therapeutic agent.

As seen in the example of FIG. 10*a*, a first porous coating 1038, an expandable member 1040, a therapeutic agent layer 1042, and a second porous coating 1044 have been loaded within the slot 1036, however, other arrangements are possible. In the example, the first porous coating 1038 may be located proximate the inner surface side 1046 of the strut while the second porous coating 1044 may be located proximate the outer surface side 1048 of the strut 1024. The expandable member in this example is a hydrophilic polymer material with a molecular weight higher than that of the therapeutic agent 1022. Examples of hydrophilic polymers include water soluble and/or swellable polymers/copolymers. For example, ionic polymers such as polyelectrolytes including polyacrylic acid, polystyrenesulfonic acid, polyvinyl sulfonic acid, hyaluronic acid, and heparin may be used. In addition, non-ionic polymers such as polyethylene oxide, polyvinyl pyrrolidone, polyacryl amide, polymethacryl amide, polyvinyl alcohol, and hydroxyl propyl methylcellulose, carboxyl methylcellulose may also used.

The first porous coating 1038 may have a pore size large enough for bodily fluids (e.g. blood and water) to pass, but may also be small enough so that none or only minimal amounts of the expandable material (e.g. hydrophilic polymer) can leak therethrough. Likewise, the second porous coating 1044 may have a pore size large enough for therapeutic agent 1022 to travel therethrough, however, the porous coating 1044 may also be small enough so that none or only minimal amounts of the expandable material may escape. Therefore, even when all of the therapeutic agent 1022 has been delivered from the slot 1036, the expandable material will be prevented or at least limited from contacting the tissue and/or bloodstream because the pores on the porous coatings 1038, 1044 on both sides of the strut 1036 are sized accordingly.

In use, as seen in FIG. 10*b*, when the medical device is positioned in vivo, bodily fluids such as water may pass through the first porous coating 1038 and may swell the expandable member 1040 (e.g., hydrophilic polymer). This expansion may eject or force the therapeutic agent 1022 out through the second porous coating 1044.

Other suitable expandable members include an osmotic pump which may be used to increase the pressure in the slot to force therapeutic agent release to the vessel wall. The osmotic pump may be comprised of a semi-permeable membrane (e.g., regenerated cellulose, cellophane, polymide, etc.) confining a material or solution with a higher affinity for water than surrounding tissue or blood. For example, a semi-permeable polyurethane membrane containing albumin and/or high concentration salt solution, as is well known in the art, may be utilized. In vivo, the osmotic pump can draw water from the body fluids and subsequently may swell. It is also contemplated by certain embodiments of the present invention that non-polymer osmotic pump structures can be fabricated from micro bellows assemblies attached to appropriate semi-permeable membrane end caps.

Other suitable expansion members may include compressible fibers and foams, for example, three dimensional compressible fibers and foams may be loaded into compressible metal and/or polymer materials to hold the therapeutic agent. Compacted SMA fibers may also be used.

Figure 11A:
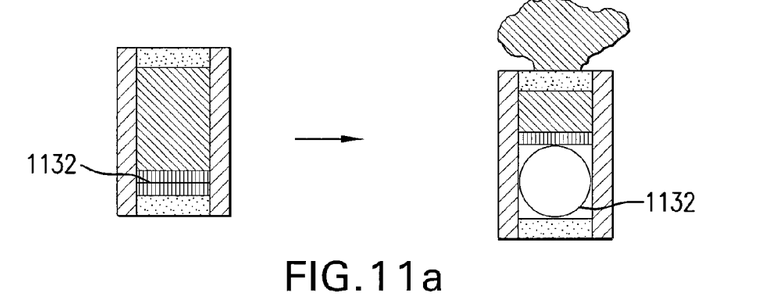
FIGS. 11a-c show enlarged cross-sectional views of various stent strut slots during therapeutic loading and release as may be employed in accordance with embodiments of the present invention.
Figure 11B:
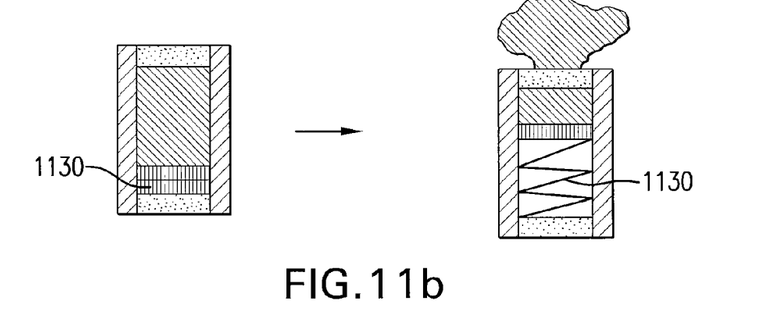
Figure 11C:
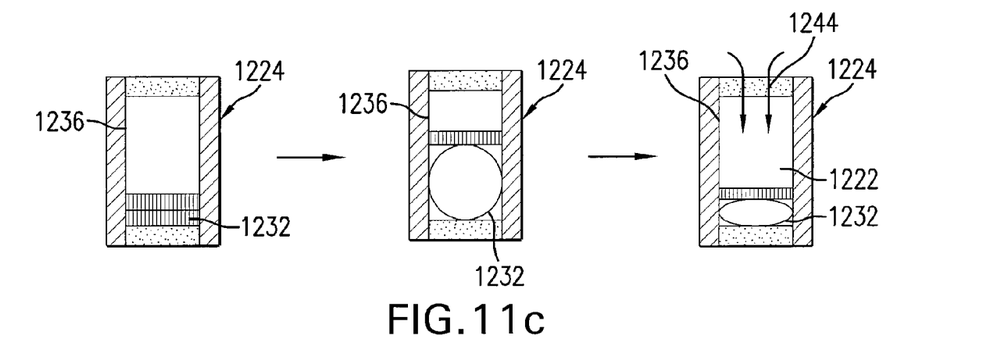

Still other suitable expansion members are shown in FIGS. 11*a-c*. FIGS. 11*a-b* show pre-shaped thermal memory alloys as the expansion members 1130, 1132. In FIG. 11*a*, a rounded tube expansion member 1132 is shown expanding when heat, such as body heat, is applied. Similarly, FIG. 11*b* shows a zig-zag shaped expansion member 1130 expanding when heat is applied.

According to embodiments of the present invention, the thermal shaped alloy may be used for one-way and two-way shape memory activation to facilitate loading and delivery of therapeutic agent in vivo. For example, FIG. 11*c* shows an example in which the thermal shaped memory activation member may be used to pull the therapeutic agent into the chamber to facilitate loading of the therapeutic agent.

In the example of FIG. 11*c*, the pre-shaped thermal memory alloy or compressed tube 1232 shown may be manufactured and utilized as follows to facilitate loading of the pores with therapeutic agent. A pre-shaped thermal memory material may have a phase transformation temperature, Af, at about 60° C., As, at about 50° C., Ms, at about −10° C., and Mf, at about −30° C. Af is the austenitic phase transformation finish temperature, As is the austenitic phase transformation start temperature, Ms is the martensitic phase transformation start temperature, and Mf is the martensitic phase transformation finish temperature. Consequently, the tube may be flattened and held in the flattened condition for several minutes, typically 5 to 10 minutes, at high temperatures of around 500° C. to set the shape. The flattened tube may then be cooled down to below about −30° C. and deformed to form a round tube, for example, such as by passing a mandrel through the tube. The tube may stay in this round shape as long as it is maintained at a temperature below about 50° C. The round tube may be placed in a slot 1236 on a strut 1224 and a second porous coating 1244 loaded on top. It is also contemplated by certain embodiments of the present invention that small diameter holes can be cut in the circumference of the tube and the tube itself may be used to contain and elute the therapeutic agent. Heating and cooling to change the tube shape from round to oval can be used to "draw in" and "push out" therapeutic agent. The porous tube structure can also be fabricated into a stand alone medical device structure.

The medical device may then be placed in a closed container which is under vacuum, for instance, to remove air from the pores to facilitate loading. A solvent with therapeutic agent 1222 can be filled in the container and heated to above about 60° C. Due to the shape memory, the tube will go back to the flattened shaped and this movement will draw the solvent/therapeutic agent 1222 into the slot 1236 through the porous coating 1244. In this example, the elution of the therapeutic agent may be achieved by diffusion and the therapeutic may be configured to dissolve in the body fluid.

Figure 12:
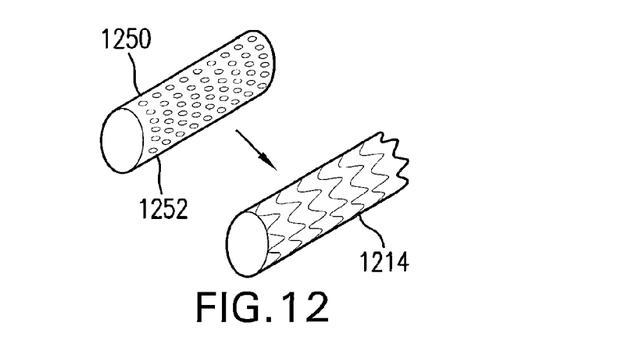
FIG. 12 shows a sleeve that may be used in accordance with embodiments of the present invention.

FIG. 12 shows a variation that may be employed in accordance with embodiments of the present invention to facilitate loading of the pores with therapeutic agent. In this embodiment, rather than cutting slots in the stent struts 1124, a sleeve 1250 may be placed over the medical device 1214. For example a nitinol sleeve 1250 may be used. The sleeve 1250 itself may have pores 1252. Suitable techniques such as photo-chemical etching and/or laser drilling may be used to form the pores 1252 on the surface of the sleeve 1250. The pores 1252 may be loaded with a shape memory material in a similar manner to that explained herein above with respect to FIG. 11*c*. After the shape memory material is expanded, the sleeve 1250 may be immersed in a solvent/therapeutic agent solution. The solution may then be heated. As the sleeve 1250 is heated within the solution, the shape memory material (e.g., 1232 in FIG. 11*a*) located in the pores 1252 of the sleeve 1252 may then contract and pull the solvent/therapeutic agent into the sleeve 1250 to load the pores 1252.

It is contemplated by embodiments of the present invention that the sleeve 1250 of the FIG. 12 may be used for one-way and two-way shape memory activation to facilitate loading and deliver of therapeutic agent in vivo.

Figure 13:
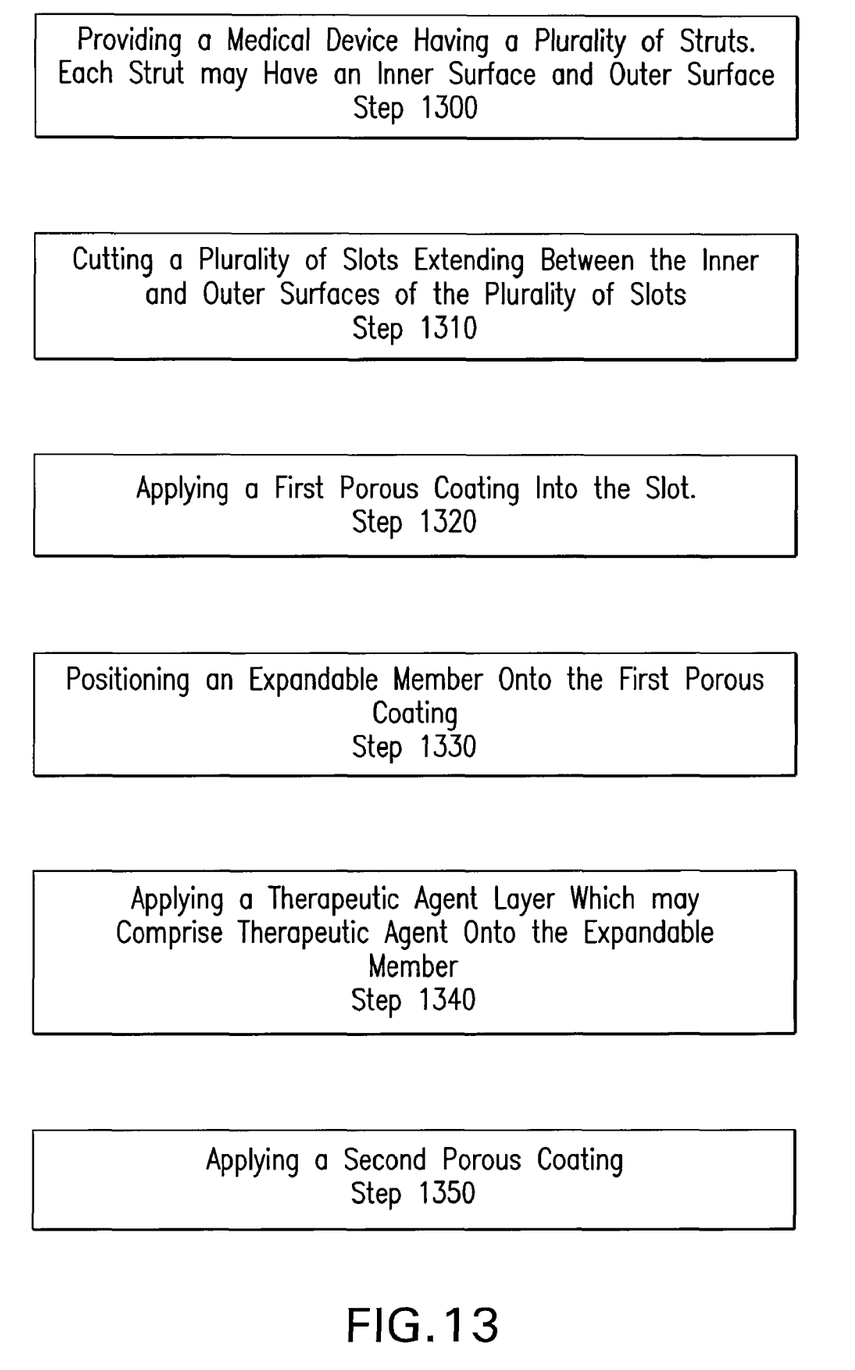
FIG. 13 shows a flow chart of a method that may be employed in accordance with embodiments of the present invention.

FIG. 13 shows a flow chart including method steps that may be employed with embodiments of the present invention. In the example of FIG. 13, step 1300 may include providing a medical device having a plurality of struts. Each strut may have an inner surface and an outer surface. Step 1310 may include cutting a plurality of slots extending between the inner and outer surfaces of the plurality of slots. Step 1320 may include applying a first porous coating into the slot. Step 1330 may include positioning an expandable member onto the first porous coating. Step 1340 may include applying a therapeutic agent layer, which may comprise therapeutic agent, onto the expandable member. Step 1350 may include applying a second porous coating over the therapeutic agent. As stated herein above, the term "slot" as used herein is meant to encompass any opening of suitable size and shape. When implanted, body heat can expand the expandable material or structure to eject the therapeutic agent.

In other embodiments, not shown, the sequence of steps may be reordered and steps may be added or removed. The steps may also be modified consistent with the invention.

While various embodiments have been described, other embodiments are plausible. It should be understood that the foregoing descriptions of various examples of the medical device and porous coatings are not intended to be limiting, and any number of modifications, combinations, and alternatives of the examples may be employed to facilitate the effectiveness of delivering therapeutic agent from the porous coating.

A suitable list of drugs and/or polymer combinations is listed below. The term "therapeutic agent" as used herein includes one or more "therapeutic agents" or "drugs." The terms "therapeutic agents" or "drugs" can be used interchangeably herein and include pharmaceutically active compounds, nucleic acids with and without carrier vectors such as lipids, compacting agents (such as histones), viruses (such as adenovirus, adenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, everolimus, zotarolimus, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. An implantable medical device for controllably releasing a therapeutic agent within a patient, comprising:
   a plurality of struts, each strut having an inner surface and an outer surface; and
   a plurality of slots extending between the inner and outer surfaces of the plurality of struts; each slot comprising:
      a first porous coating located proximate the inner surface of the strut;
      an expandable member located proximate to the first porous coating;
      a therapeutic agent layer comprising therapeutic agent located proximate to the expandable member; and
      a second porous coating located proximate the outer surface side of the strut proximate to the therapeutic agent layer,
   wherein in vivo bodily fluids first pass through the first porous coating and then contact and expand the expandable member so that the expandable member forces the therapeutic agent into the second porous coating.

2. The device of claim 1 wherein the porous coatings are configured to prevent portions of the expandable member from passing therethrough.

3. The device of claim 1 wherein the expandable member is formed of a hydrophilic polymer material.

4. The device of claim 1 wherein the expandable member is a semi-permeable osmotic pump.

5. The device of claim 1 wherein the expandable member is a pre-shaped thermal memory alloy.

6. The device of claim 1 wherein the expandable member is a three dimensional fiber or foam.

7. The device of claim 1 wherein at least one of the plurality of slots extends entirely through its respective strut of the plurality of struts.

* * * * *